United States Patent [19]

Shoesmith

[11] Plant 4,290

[45] Aug. 8, 1978

[54] CHRYSANTHEMUM NAMED BRITISH GOLD

[75] Inventor: Leonard H. Shoesmith, Westfield-Woking, England

[73] Assignee: Pan-American Plant Company, West Chicago, Ill.

[21] Appl. No.: 783,012

[22] Filed: Mar. 30, 1977

[51] Int. Cl.[2] ..... A01H 5/00

[52] U.S. Cl. ..... Plt./78

[58] Field of Search ..... Plt./78

*Primary Examiner*—Robert E. Bagwill

*Assistant Examiner*—James R. Feyrer

*Attorney, Agent, or Firm*—Chas. W. Rummler

[57] ABSTRACT

A new and distinct variety of chrysanthemum plant for greenhouse culture characterized by the golden bronze color of the ray florets of its medium size flowers and its decorative flower form which does not reflex, its 10-week photoperiod response, its spreading pot plant habit with an abundant production of small to medium size foliage, and its very good breaking ability when manually pinched.

2 Drawing Figures

BACKGROUND OF THE NEW PLANT

My new variety of chrysanthemum plant was discovered by me in 1972 as a seedling of unidentified parentage growing among breeding stock in my greenhouse at Westfield-Woking, Surrey, England. The golden bronze coloring of the flowers attracted my fancy and by cuttings from the original plant, I produced several reproductions of the plant in my greenhouse to observe and test its growth and flowering characteristics. The results proved favorable and demonstrated that the new plant has novel and commercially valuable characteristics and my propagation of the new plant through several successive generations by means of vegetative cuttings, at Westfield-Woking, Surrey, England, has demonstrated that its distinctive characteristics hold true from generation to generation and appear to be firmly fixed.

Commercial scale propagation of my new plant is now being done at West Chicago, Ill., and at Cortez, Fla., with faithful retention of the novel characteristics of the original plant.

DESCRIPTION OF THE DRAWINGS

This new chrysanthemum plant is illustrated by the accompanying drawings, the first being a photographic drawing which in full color shows the flowers and foliage of a potted plant in full bloom and the second drawing being a reproduction of a mechanical print of representative leaves of the new plant taken at several levels along a stem to show their distinctive form. The colors shown in the photographic drawing are as nearly true as it is possible to obtain by conventional photographic procedures. The photograph was made in September, 1976.

DESCRIPTION OF THE NEW PLANT

The following is a detailed description of my new chrysanthemum plant based upon observations at West Chicago, Ill., and with color designations according to the R.H.S. Colour Chart published by The Royal Horticultural Society of London, England, in collaboration with The British Colour Council.

THE PLANT

Origin: Seedling.

Parentage: Both seed parent and pollen parent are unidentified chrysanthemum varieties.

Classification:

*Botanic.*—*Chrysanthemum morifolium.*

*Commercial.*—Greenhouse pot plant.

Form: Perennial herbaceous bush.

Height: 11 to 15 inches.

Growth: Terminal. Vigorous and upright, sturdy and with very good strength.

Branching: Normal under natural conditions.

Foliage: Quantity — Abundant with 8 to 10 leaves per 4 inches of stem.

*Leaf size.*—$2\frac{1}{8}$ to $3\frac{1}{4}$ inches long and $1\frac{1}{4}$ to $1\frac{3}{4}$ inches wide.

*Leaf shape.*—Lobed — lanceolate with slightly serrated margin.

*Surface aspect.*—Canescent.

*Color.*—Upper side — RHS 147A. Under side — RHS 147B to 148A.

*Venation.*—Leaves are pinnately veined.

*Petioles.*—$\frac{1}{8}$ to $\frac{1}{2}$ inch long.

THE BUD

Form: Globular.

Size: $\frac{1}{2}$ inch in diameter and $\frac{1}{4}$ to $\frac{3}{8}$ inch deep.

Opening rate: Slow.

Color:

*When phyllaries first divide.*—RHS 144A.

*When florets begin to unfurl.*—RHS 15A, 17A, 17B.

Phyllaries: The outside of the receptacle bears many involucral spear-shaped and upstanding bracts.

*Color.*—Inside — RHS 146C. Outside — RHS 147C.

*Surface aspect.*—Pubescent.

Peduncle: Erect and $\frac{3}{4}$ to $1\frac{1}{4}$ inches long.

*Surface aspect.*—Pubescent.

THE FLOWER

Recommended flowering: Year around.

Response: 10-week.

Natural flowering season: November 3 to November 10.

Blooms: Flower type — composite and decorative.

*Borne.*—A head of many florets on a receptacle.

*Size.*—Medium. Diameter —$2\frac{5}{8}$ to 4 inches. Depth — $1\frac{1}{4}$ to $1\frac{3}{4}$ inches.

*Shape.*—Flat from the time the bloom first opens.

*Florets.*—Number — Numerous. Form: Linear with obtuse apex.

| Color : (RHS) Flowering Period | Feb. | Mar. | April | October |
|---|---|---|---|---|
| Outer Florets : | | | | |
| Upper side | 14A | | 17A | 14A, 14B |
| Reverse side | 13B | 11A | 15B | 13A, 13B |
| Inside Florets : | | | | |
| Upper side | 13B | | 17A | 14A |
| Reverse side | | 17B | 15B | 13A, 14B |

*Firmness.*—Medium.

*Appearance.*—Very slightly shiny.

*Discoloration.*—Very slight fade after full bloom.

Peduncle: Sturdy and upright. Length — $\frac{3}{4}$ to $1\frac{1}{4}$ inches.

*Color.*—RHS 147B.

Persistence: Florets hang on and dry.

Fragrance: Typical chrysanthemum.

Lasting quality: 3 weeks on the plant.

REPRODUCTIVE ORGANS

Stamens:

*Arrangement.*—5 syngenesious stamens.

*Filaments.*—1/16 to $\frac{1}{8}$ inch long. Color: Light yellow.

*Pollen.*—Yellow.

Pistils:

*Number.*—One for each ray and disc floret.

*Styles.*—$\frac{1}{8}$ *to* 3/16 inch long.

*Stigmas.*—Color — Yellow.

Ovaries: Inferior bicarpellate.

This chrysanthemum plant is not recommended for cut flowers or other than greenhouse culture. Its distinctiveness resides in the golden bronze coloration of its blooms and its decorative flower form which does not reflex, its medium to tall vigor, sensitivity to low soil aeration, spreading pot plant habit, and very good breaking ability which produces 4 to 6 lateral breaks when manually pinched. This plant is capable of being flowered the year around with a normal 10-week response, subject to occasional delay when exposed to low or high greenhouse temperatures, and has a sensitivity to low soil aeration with respect to growth.

I claim:

1. A new and distinctive chrysanthemum plant, substantially as herein shown and described, characterized by the golden bronze coloring of its medium size flowers the form of which does not reflex, the medium to tall vigor of the plant growth, and its spreading pot plant habit with a very good breaking ability when manually pinched.

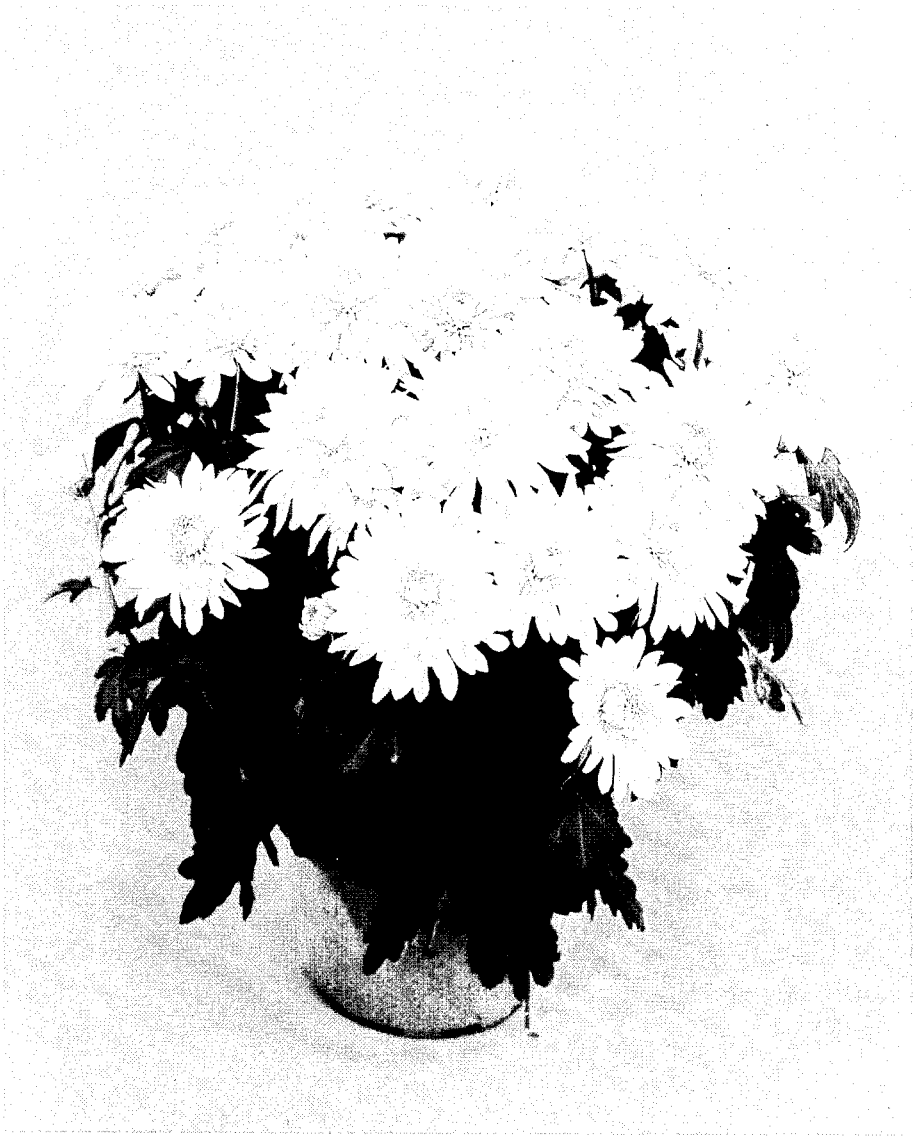

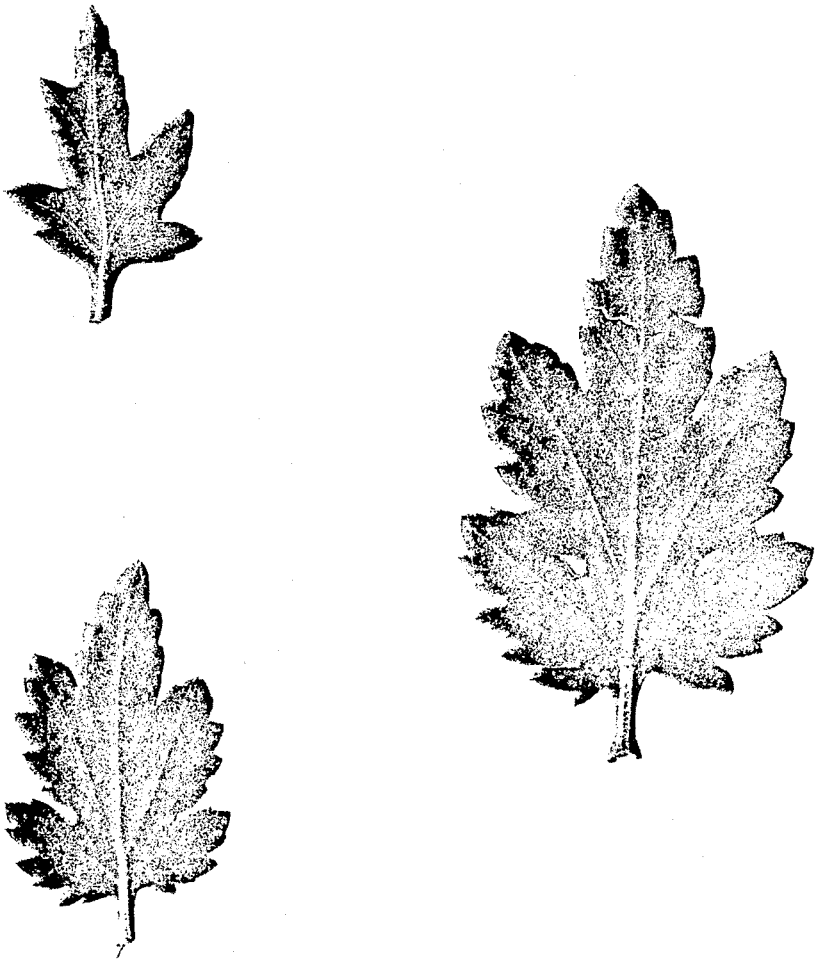

* * * * *